United States Patent
Rice et al.

(10) Patent No.: US 10,528,834 B2
(45) Date of Patent: Jan. 7, 2020

(54) BIOMETRIC SENSOR FOR DETECTION OF WRIST BLOOD VESSELS IN A WRISTWATCH OR WRISTBAND

(71) Applicant: Biowatch SA, Martigny (CH)

(72) Inventors: Joseph Rice, Notthingham (GB); Matthias Vanoni, Montreux (CH)

(73) Assignee: Biowatch SA, Martigny (CH)

( * ) Notice: Subject to any disclaimer, the term of this patent is extended or adjusted under 35 U.S.C. 154(b) by 217 days.

(21) Appl. No.: 15/046,155

(22) Filed: Feb. 17, 2016

(65) Prior Publication Data

US 2016/0267338 A1    Sep. 15, 2016

(30) Foreign Application Priority Data

Mar. 13, 2015   (EP) .................... 15158950

(51) Int. Cl.
| | |
|---|---|
| *G06K 9/00* | (2006.01) |
| *A61B 5/00* | (2006.01) |
| *A61B 5/1171* | (2016.01) |
| *A44C 5/18* | (2006.01) |
| *G01J 1/02* | (2006.01) |
| *G01J 1/42* | (2006.01) |
| *G01J 1/44* | (2006.01) |

(52) U.S. Cl.
CPC ............ *G06K 9/00885* (2013.01); *A44C 5/18* (2013.01); *A61B 5/1171* (2016.02); *A61B 5/681* (2013.01); *G01J 1/0204* (2013.01); *G01J 1/0238* (2013.01); *G01J 1/0271* (2013.01); *G01J 1/4228* (2013.01); *G01J 1/44* (2013.01); *G01J 2001/0257* (2013.01); *G06K 2009/00932* (2013.01)

(58) Field of Classification Search
None
See application file for complete search history.

(56) References Cited

U.S. PATENT DOCUMENTS

| | | | |
|---|---|---|---|
| 4,699,149 A | 10/1987 | Rice | |
| 6,799,726 B2 | 10/2004 | Stockhammer | |
| 7,174,032 B2 | 2/2007 | Takiguchi et al. | |
| 8,019,126 B2 | 9/2011 | Amano | |
| 8,570,148 B2* | 10/2013 | Amano | A61B 5/0059 340/5.82 |
| 2002/0183624 A1 | 12/2002 | Rowe et al. | |
| 2003/0173408 A1* | 9/2003 | Mosher, Jr. | A61B 5/117 235/492 |
| 2008/0081968 A1* | 4/2008 | Numada | A61B 5/02007 600/322 |

(Continued)

FOREIGN PATENT DOCUMENTS

EP    2328111 A1    6/2011

OTHER PUBLICATIONS

S. Cassidy, "Business Technology; A Card That 'Sees' User's Veins", NYTimes.com; 1988; pp. 1-3.

(Continued)

*Primary Examiner* — Bernard Krasnic
(74) *Attorney, Agent, or Firm* — Blank Rome LLP (57) ABSTRACT

A biometric sensor for detecting wrist blood vessels in a wristband or wristwatch. The sensor has a substrate and an array of thermal detectors arranged on the substrate. Suitable detectors include near infrared photodetectors or temperature detectors. Advantageously, the array has printed organic components on the substrate.

19 Claims, 4 Drawing Sheets

(56) References Cited

U.S. PATENT DOCUMENTS

| | | | |
|---|---|---|---|
| 2009/0005661 A1* | 1/2009 | Ozawa | A61B 5/1455 600/322 |
| 2009/0169078 A1* | 7/2009 | Ozawa | A61B 5/0059 382/128 |
| 2010/0100160 A1 | 4/2010 | Edman et al. | |
| 2010/0130841 A1* | 5/2010 | Ozawa | A61B 5/681 600/323 |
| 2011/0034912 A1 | 2/2011 | de Graff et al. | |
| 2013/0041235 A1 | 2/2013 | Rogers et al. | |
| 2013/0314303 A1* | 11/2013 | Osterhout | G06F 3/005 345/8 |
| 2014/0107493 A1* | 4/2014 | Yuen | H04W 4/027 600/473 |
| 2014/0196131 A1 | 7/2014 | Lee | |
| 2015/0366518 A1* | 12/2015 | Sampson | A61B 5/7221 600/301 |
| 2016/0029778 A1* | 2/2016 | Fitzgerald | A45F 5/02 224/272 |

OTHER PUBLICATIONS

J. Rice, "A Third Way for Biometrics [long]", Google Groupes, Mar. 29, 1999, pp. 1-5.

J. Rice, "The Future of Vein Recognition", Biometrics, Apr. 2001, pp. 1-4.

* cited by examiner

BIOMETRIC SENSOR FOR DETECTION OF WRIST BLOOD VESSELS IN A WRISTWATCH OR WRISTBAND

RELATED APPLICATION

This Application claims priority of European Patent Application EP15158950.4 filed on Mar. 13, 2015, the contents of which is incorporated by reference.

FIELD OF THE INVENTION

The present invention concerns a biometric sensor for detection of wrist blood vessels in a wristwatch or wristband, and a wristwatch with such a sensor.

DESCRIPTION OF RELATED ART

Biometrics is widely used in order to authenticate or identify users. Biometrics is often based on fingerprint, voice, retina, iris, palm, face or wrist vessel recognition. The present application is related to biometric sensors used for authenticating or identifying users based on patterns of blood vessels in the wrist.

The subcutaneous blood vessels on a human wrist can be imaged using infrared illumination and in particular, near infrared (NIR) illumination. It has already been suggested to authenticate users by capturing near infrared images of a wrist vein pattern with a sensor in a wristwatch.

This technology is disclosed, among other, in an article published by the New York Times and related to a smart card carrier that reads veins. The article is available at http://www.nytimes.com/1988/12/14/business/business-technology-a-card-that-sees-user-s-veins.html.

An oral presentation on this subject was also made by Mr Joe Rice at the Biometric Summit in Washington, D.C. in January 1999. This lecture was subsequently published in the Information Systems Audit and Control Associations Journal, and is available at https://groups.google.com/forum/#!msg/comp.society.privacy/gynQOQHXzmQ/6LpJubLOWmwJ.

The web page "http://fingerchip.pagesperso-orange.fr/biometrics/types/vein_JoeRice.htm" describe another aspect of vein pattern biometric and how it can be applied to safeguarding the individuals privacy and security.

U.S. Pat. No. 8,019,126B2 describes a biometric data acquisition device to be worn around the wrist. The device comprises a biometric acquisition unit for acquiring a vein pattern of a living body, and an authentication unit for performing personal authentication using the vein pattern acquired by the biometric acquisition unit. The biometric data acquisition unit includes a light source unit that emits illuminating light, such as a LED or a circular light source unit, and a light receiving unit such as a CCD device and micro lens arrays provided on one main surface of the circular basis of the wristwatch. This document does not describe the technology used to manufacture the light source unit and the CCD device. Conventional technology would result in a thick, flat device that is difficult to integrate in a wristwatch, especially in a flat wristwatch. Moreover, large CCDs which are required in order to scan a large area of the dorsal area of the wrist are expensive and power-consuming.

U.S. Pat. No. 6,799,726B2 describes a wristwatch having a biometric sensor positioned so as to rest on the skin and detect the subcutaneous pattern or arteries, veins, capillaries and other blood vessels. The technology used to manufacture the sensor is not described.

U.S. Pat. No. 7,174,032B2 describes an apparatus with a pickup section for picking up an image of a blood vessel pattern of a wrist. The pickup section is provided with a near-infrared LED an IR camera, such as a CCD camera. The apparatus is voluminous and intended to be integrated in a chair armrest.

U.S. Pat. No. 4,699,149 discloses an apparatus for identifying an individual based on his detected blood vessels. The apparatus comprises infra-red radiation emitting diodes and reflecting radiations sensing means.

US20140196131 discloses a wearable wrist vein pattern device for authentication applications. The wrist device comprises illuminators, such as LEDs or VCSELs Lasers, and an array of wrist contact sensors, e.g. CCD sensors.

EP2328111 describes a biometric pattern detecting method and device adapted to detect subcutaneous blood vessels for authentication applications. The device exploits optical, electrical and/or temperature discriminants between epidermal tissue and deep-layer tissue of the skin. In one embodiment, tissue structures are established by a plurality of temperature detecting devices arrayed upon the skin. A two-dimensional array of detecting temperature devices, e.g. thermistor, bolometers, thermopiles, is arranged to detect epidermal layer temperatures.

US2013041235 describes a biomedical device for sensing and actuation application that comprise electronic circuit silicon based designed for being affixed to the skin or onto an organ.

Similarly, US2011034912 discloses a silicon based biomedical device enabling conformal sensing contact with tissues of interest, such as the inner wall of a lumen, the brain, or the surface of the heart.

US20100100160 provides a device for adjusting phototherapeutic intervention. The device comprises light sources and detectors for treating a specific region of a body.

US20020183624 describes an apparatus capable of being inserted in a wristwatch for the purpose of providing secure biometric access to protected property.

A problem common to prior art devices for sensing patterns of blood vessels in the wrist is their thickness which make them difficult to integrate in a wristwatch or bracelet for a wristwatch. It would be desirable to have a thickness of the biometric sensor below 5 mm, preferably below 3 mm.

Another problem is the cost of designing and manufacturing sensors in various different dimensions. Wristwatches and bracelets exist in a large variety of sizes and forms, and it would be desirable to adapt the size and form of the sensor to each specific design. However, the cost of producing small series of devices using conventional photolithography technologies is prohibitive.

Another aim is to use a technology which is scalable and could also be used for a mass production, for example several millions a year, at a reasonable cost.

Most existing photodetectors are based on semiconductor material such as germanium or silicon. In particular, silicon photodiodes and photodetectors based on metal-oxide silicon capacitors are widespread and easy to product in quantities. However, the maximal size of sensors based on array of photodiodes produced with those technology is limited. It would however be desirable to have sensors able to image a large surface of the skin, for example an image of 3×3 $cm^2$ or preferably 4×4 $cm^2$.

It has been suggested to use amorphous-silicon based sensors in order to produce large size sensors. However, this technology limits the detection of light below 800 nm, which is problematic for the detection of blood vessels below the surface of the skin. Furthermore, the micro-fabrication steps necessary for the manufacture of such a detector would be difficult to realize on a bendable substrate.

BRIEF SUMMARY OF THE INVENTION

According to the invention, these aims are achieved by means of a biometric sensor for detecting wrist blood vessels in a wristband or wristwatch, said sensor comprising a substrate and an array of thermal detectors on said substrate, such as near infrared photodetectors or temperature detectors, wherein said array comprises printed organic components on a substrate.

The use of printed organic technology for producing the sensor reduces the thickness of the sensor. This reduction is due to the thin substrate that could be used and to the fact that printed electronic components do no need encapsulation.

Printed electronics incorporates novel fabrication methods that use printing techniques. The metallic layers are developed with nanoparticles-based inks (silver, gold, etc.) using digital printing (inkjet printing) or conventional printing (screen, gravure, flexo printing) to form the desire patterns.

Organic components can be printed on large area. Therefore, sensors can be produced which are able to image a large area of the skin, even when in direct contact or at close distance.

The use of printed electronics further allows for the design of small series of sensors, for example sensors in dimensions, shapes and resolution adapted to various watches or wristbands.

The sensor may further use printed transistors.

In one embodiment, the sensor comprises one layer of photodetectors, for example photodetectors able to convert incoming light in the infrared near-infrared range into a current. Infrared and near-infrared photodetectors are called thermal detectors since the amount in infrared and near-infrared light emitted by a body depends on its temperature.

In one embodiment, the sensor comprises one layer of photodetectors on a first substrate, and a second layer of transistors on a second substrate, the two substrates being superimposed.

The substrate may be flexible. The substrate may be made of plastic.

The substrate may be curved, and thus adapted to the shape of the wristwatch, of a part of the wristband such as the clasp, and/or to the wrist.

The thermal detectors may comprise near-infrared organic photodetectors, i.e., detectors that convert incoming photons in the near-infrared band into an electric current.

Organic photodetectors can be tuned over a wide wavelength range by carefully choosing the active material. Therefore, this technology allows for the production of photodetectors able to detect light in different, selectable wavelength ranges.

The thermal detectors being adapted for capturing a plurality of images captured in a plurality of different wavelengths. For example, a first image may be captured in a first frequency range, such as near-infrared range, and a second image may be simultaneously captured in a different frequency range, such as for example visible range.

In this application, the expression "image" should be given a broad meaning so as to encompass different concepts. An image could be a picture or reproduction, for example on paper or on a display. An image could be data corresponding to such a reproduction, for example a file such as a tif file, a jpeg file etc. An image could correspond to a visible phenomenon, for example a reproduction in a visible range of what a human or visible length sensor would see, or to something not visible, for example data or reproduction of values captured by a sensor such as an infrared sensor, a near-infrared sensor, a temperature sensor, etc.

The sensor may further comprise illumination LEDs or OLEDs.

The illumination OLEDs may be produced with printed technology, or produced with thin-film optics.

The biometric sensor may comprise a pattern of illumination LEDs or OLEDs and photodetectors. For example, the sensor may comprise a matrix of illumination LEDs or OLEDs mixed with photodetectors, or lines of photodetectors separated by lines of illuminating LEDs or OLEDs.

The sensor may be adapted for capturing near-infrared images of the wrist when directly in contact with the skin. It has been shown that the contrast between blood vessels, such as veins, that absorb part of the incoming light, and the surrounding tissues that reflect a higher amount of the light, is good at those wavelengths, i.e., between 750 nm and 850 nm. This wavelength range allows scanning a deeper depth of human tissues compared to visible wavelength, providing access to a larger number of blood vessels, and in return a larger number of points for personal identification which leads to increased security.

The sensor may be adapted for the detection of light in different ranges of wavelength, for example in the near-infrared range and in the visible range. This might be useful for detecting even more blood vessels. This might also be used for preventing spoofing, since it is more difficult to manufacture or print an artefact that reflects light in different wavelength range in a manner similar to the human body.

The sensor may be adapted for capturing near-infrared images of the wrist from a distance of at least several millimetres to the skin.

The sensor may comprise an array of optical lenses for focusing images of the skin onto the photodetectors at a distance.

The optical lenses may be made of printed elements.

The thermal detectors may comprise temperature detectors, such as resistive temperature detectors.

The present invention is also related to a wristwatch or wristband comprising such a biometric sensor.

The biometric sensor may be mounted on the back of the wristwatch for detection of blood vessels on the outer side of the wrist.

The biometric sensor may be mounted on the inner side of a bracelet or clasp for detection of blood vessels on the inner side of the wrist.

The wristwatch or wristband may comprise a processor for processing the image data measured by said sensor in order to identify or authenticate a user.

A software module may be executed by the processor for causing said processor to stitch data corresponding to different portions of the wrist, in order to retrieve a pattern of blood vessels over an area larger than the area covered by said array of detectors. In this case, an image of a large portion of the wrist may be retrieved by sliding the sensor against or at a distance from said wrist, and assembling a plurality of successively captured images onto a large size image.

A plurality of successive measures of the wrist may be combined in order to retrieve a more precise pattern of blood vessels, for example by increasing resolution or averaging a plurality of measures of a single point.

A plurality of successive measures of the wrist may be analysed for verifying the aliveness of the user, for example by detecting pulse.

The invention is also related to a method of manufacturing a biometric sensor for detecting wrist blood vessels, comprising;

providing a substrate;

printing an array of thermal detectors on said substrate, such as infrared photodetectors or temperature detectors.

The step of printing may comprise depositing successive layers of inks using digital printing, for example using ink-jet technology.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 1:
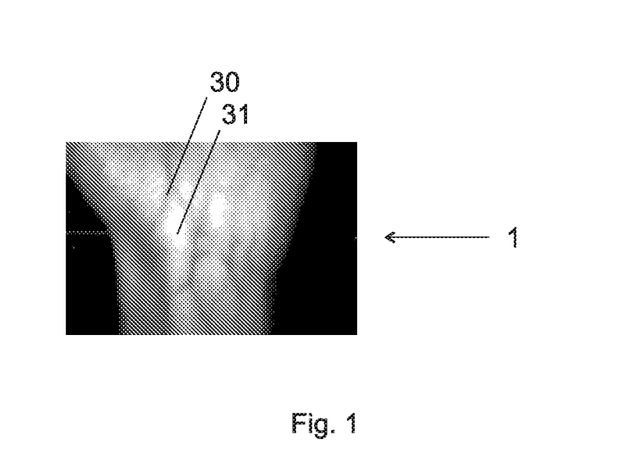
FIG. 1 shows an image of a pattern of blood vessels in a human wrist.

FIG. 1 illustrates an image 1 of the inner side of a human wrist captured with a common CCD camera. It shows a pattern of blood vessels 30, in particular veins, clearly distinguishable among the surrounding tissues 31. In one example, this image is a reproduction in the visible range of data captured with a near-infrared or temperature sensor. This pattern constitutes a unique feature of the person and could be compared with one or a plurality of reference patterns in order to identify or authenticate this person.

Figure 2:
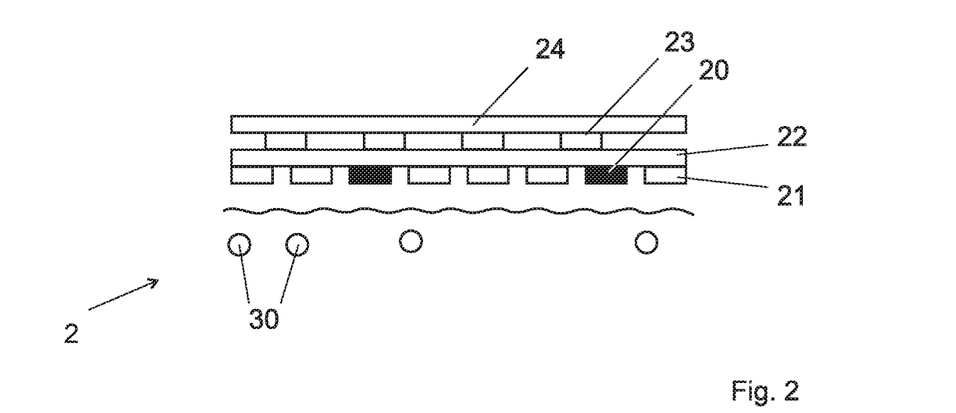
FIG. 2 is a schematic view of a sensor according to the invention.

FIG. 2 illustrates a first embodiment of a sensor 2 able to image a portion of a wrist, for example on the inner side in order to produce an image similar to the one shown on FIG. 1, or on the outer side of the wrist. This sensor could for example be integrated in the back of a wristwatch, on the inner side of the band, on the inner side of the clasp, or on the inner side of a wristband. In this embodiment, the sensor is adapted for capturing images of the skin when in direct contact with the skin 3, or at a close distance from the skin, for example at less than 5 mm from the skin.

The sensor 2 comprises a substrate 22, for example a bendable substrate, preferably a plastic substrate. Organic photodetectors 21 are printed on this substrate, for example using ink-jet or other digital printing technology. These photodetectors are adapted for capturing light reflected by the skin in one or a plurality of wavelengths, for example in the near-infrared range. Different photodetectors onto the same substrate 22 may be adapted for detecting light in different wavelengths.

The sensor comprises a second substrate 24, for example another plastic bendable substrate, onto which thin film transistors 23 are deposited or printed. These transistors are connected with the organic photodeteetors 21 in order to build a matrix comprising a plurality of rows and columns of photodetecting cells.

The sensor may comprise one or a plurality of illuminating elements. In the illustrated embodiment, the sensor comprises organic LEDs 20 embedded into the matrix of organic photodetecting cells 21, forming a pattern, such as lines or a matrix, into this sensor. Therefore, the light is emitted directly onto the surface, or close to the surface of the skin, perpendicular to the skin, and thus only needs to cross a small thickness of skin before being reflected. This reduces the power needed for illuminating the lights. The OLEDs may furthermore be pulsed in order to reduce furthermore the power consumption. Different lighting elements may be provided for different wavelengths. Additionally, or alternatively, other light elements may be provided around the sensor 2, for example additional LEDs or OLEDS for lighting in a more oblique direction, and/or optical fibres. Lighting element may also be provided on different substrate than the first substrate 22, for example on the second substrate 24, or on a dedicated substrate. The OLEDs may be printed with printed electronic technology.

In one embodiment, the skin is illuminated with light injected into a preferably flat light transmitive plate or foil acting as a light guide over or around or beneath the sensor 2. A light source injects light into the plate, which is internally reflected against the upper and lower surfaces. The upper and lower surfaces of the plate are structured with a grating in order to control the inner reflexions at the interface between the plate and the air, so as to control the intensity of light which is internally reflected or scattered outside the plate to illuminate the skin. The plate may be flat or bended. The image of the skin may traverse the plate and reach the sensor.

The illuminating sources are preferably arranged such that light emanating from the illuminating sources coincide at a depth 3 mm below the surface of the skin to minimise back scatter into the photo diode array and to optimally illuminate the veins.

In one embodiment, the illuminating sources are switched to provide a series of differently illuminated images which is integrated into a combined image to improve vein rendition.

Figure 3:
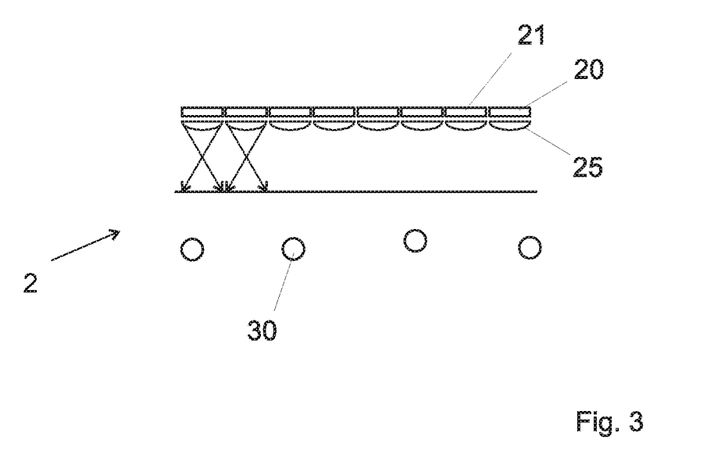
FIG. 3 is a schematic view of a sensor with an array of lenses according to the invention.

FIG. 3 illustrates another embodiment of a sensor based on photodetectors 21. This embodiment is similar to the one of FIG. 2, and could comprise the same arrangement of parts. Additionally, it comprises an array of micro lenses 25 in front of the photodetectors 21, arranged for focusing light from a distance onto the photodetectors. Therefore, this arrangement allows the capture of images from a distance, for example a distance larger than 3 mm from the surface of the skin. It is therefore possible to capture a larger area of the skin with a single sensor.

The number and disposition of lenses 25 in the array could correspond to the number and disposition of photodetectors 21. In this case, one micro lens is provided in front of each photodetector. Alternatively, the number of lenses 25 could be smaller than the number of photodetectors 21. In this case, one lens could correspond to a plurality of adjacent photodetectors, including phototodetectors working in different frequency ranges.

The array of photolenses could be produced by printing, for example 3D printing. The array may be bendable in order to adapt its shape to the sensor and to the wristwatch.

FIGS. 4 to 7 illustrate another example of sensor 2 in which each cell 27 comprises a resistive temperature detector, for mapping the temperature of the skin below the sensor.

Figure 4:
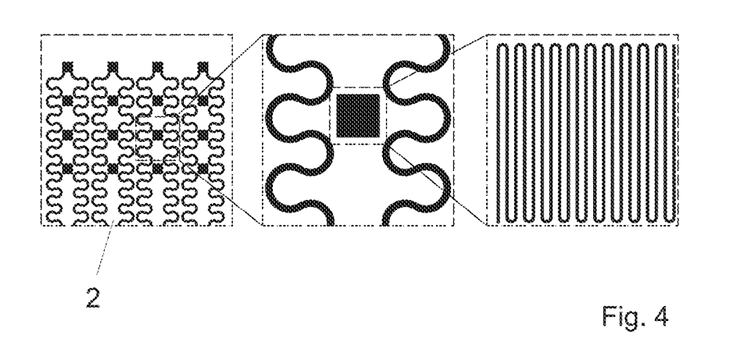
FIG. 4 is a schematic view of a resistive thermal detector.

In the example of FIG. 4, the sensor 2 comprises serpentines in order to increase the resistance value and be able to measure it with standard electronics, especially the absolute change when the temperature is varied.

Figure 5:
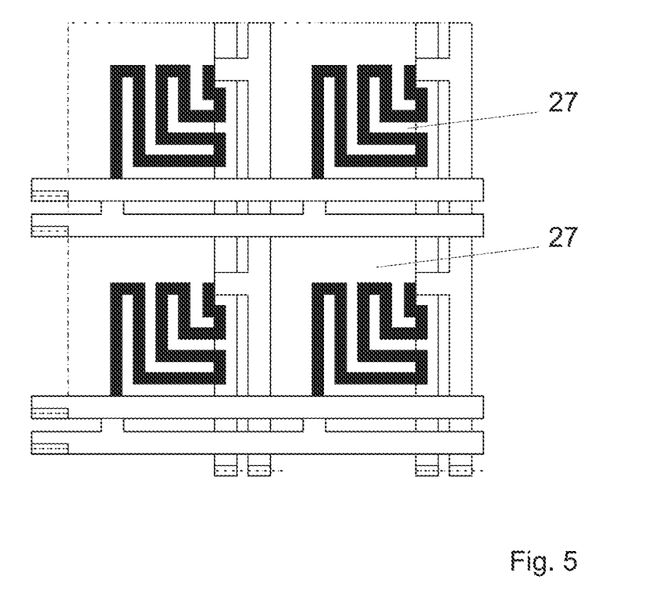
FIG. 5 illustrates four cells of a resistive thermal detector.
Figure 6:
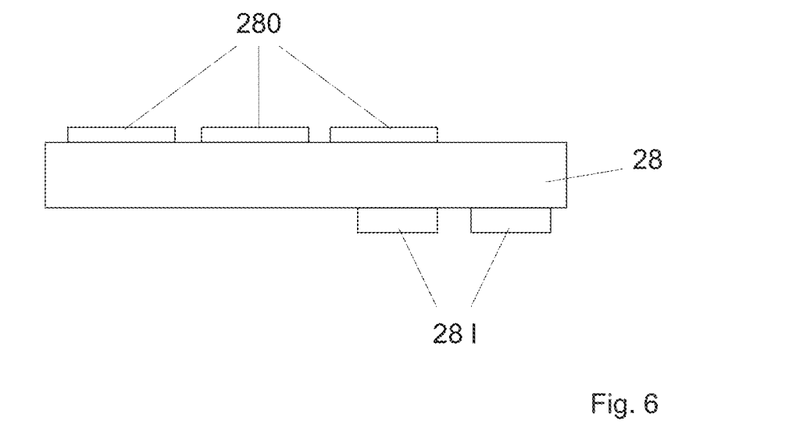
FIG. 6 illustrates a cut of one resistive thermal detector.

FIG. 5 shows an example of design of four sensor cells and how they are interconnected. The surface of each sensor cell could be comprised between 0.1 and 4 mm$^2$, for example 1×1 mm$^2$. The whole sensor could comprise at least 16 cells, for example 64 or 256 cells. The temperature measured by each cell depends on the temperature of the skin below the cell, and thus on the presence or absence of blood vessel below the cell.

Four point measurement will be realized in order to get rid of the influence of the interconnections. Two different configurations are illustrated: the first one shown on FIG. 6 makes use of a top (280) and bottom (281) metallic layer for the interconnections, with VIAS interconnection through the polymeric substrate 28. A second configuration (not shown) uses only one side of the substrate 28, which from the fabrication point of view is simpler, but it requires the deposition of a dielectric layer in between the metallic layers. Finally, FIG. 9 shows another example of sensor comprising a large number of cells organised in rows and columns.

Figure 7:
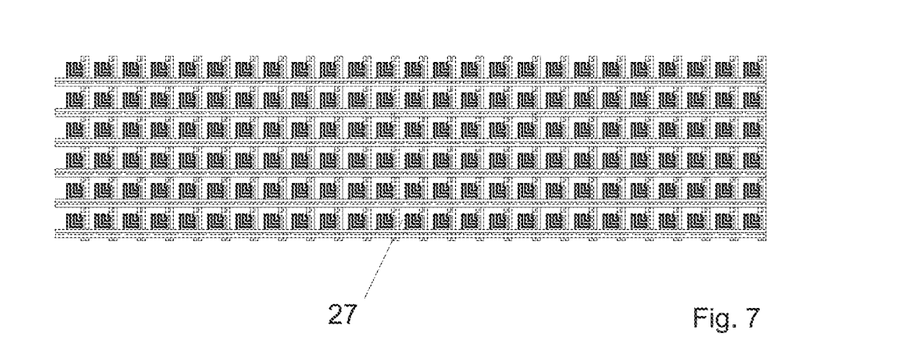
FIG. 7 illustrates a matrix of temperature sensors.

The sensor matrix is protected with a layer of PI (1.2 μm-thick) on each side, in order to provide electrical insulation and moisture barrier. The matrix is capable of take measurements at a sample of 2 Hz, with a precision of 23 mK, similar to a state of the art infrared camera. The response time of each sensor is 5 to 13 ms.

The resistive temperature sensor could be manufactured with conventional fabrication techniques, such as evaporation of metals and photolithography involving the use of expensive clean room facilities. In a preferred embodiment, this sensor is produced by printing the temperature-dependent resistive material, interconnecting lines, and transistors, onto a substrate, such as bendable substrate, for example a plastic substrate, using digital printing technology.

The reliability of the identification or authentication task depends on the number of distinguishing identification points in the captured image. Therefore, a high resolution image of a large portion of the user's wrist enables a more reliable recognition than a low resolution and/or small size image. As previously indicated, a large size image could be captured with a large size sensor against the skin, or at a distance to the skin. Alternatively, it is also possible to capture a series of images of adjacent portions of the wrist, and to assemble or stitch those successive images into a large size image corresponding to a larger portion of the wrist. The wristwatch and the sensor are preferably moved, for example slid, between each image in the series. The wristwatch, for example the clasp, could comprise a sliding guide for displacing the sensor relative to the skin and to the rest of the wristwatch, and thus facilitating this sliding movement.

In one embodiment, the sensor comprises a single line of pixels, or a thin array of pixels with a few lines (for example less than 50 lines, for example less than 10 lines) which are slid over the wrist to capture an image of a larger portion. For example, the sensor could comprise one or a limited number of lines of printed thermal detectors, possibly between two lines of near infrared LED illuminating diffusers.

The sensor maybe fronted by polarizing and wratten filters to remove environmental light and a plastic linear Fresnel lens to focus the camera on subcutaneous features.

It is possible to include two linescan cameras one in the visible to pick up the surface features of the wrist and the other in the infrared to pick up the subcutaneous features, possibly with corresponding Fresnel profiles above each.

The whole optical assembly and housing may have a curved surface so it sits snugly on the inside of the wrist and fits typical wrist profiles. It may be possible to have a conformable array so that it shapes to fit the user's wrist.

The wristwatch could also comprise a plurality of sensors for capturing images of different portions of the wrist. For example, one sensor could be provided in the back of the watch, and another sensor in the band or in the clasp.

One advantage of two sensors capturing a same portion of the skin is that one can subtract one image scan from another to render exclusively subcutaneous or surface information plus one can merge the two into a combined image.

The wristwatch could also comprise a conventional or near-infrared CCD sensor for capturing a large portion of the wrist from a distance, for example from a distance of more than 10 mm. This sensor could be triggered when the band is closed for example. It could be included into the wristband or into the clasp. The large size image captured with this sensor could be combined or compared with smaller size images captured with a different sensor in direct contact or at a small distance from the skin. In one embodiment, a single image, or a small number of images, from a large portion of the wrist is captured with one sensor at a distance from the skin, for example when the band is closed or on request from a program executed by a processor in the watch. A series of images of a smaller portion is then captured continuously or at least over a longer period with the other sensor in direct contact or at small distance from the skin. This second sensor could then be used to confirm the aliveness of the user, and to confirm that the pattern of blood vessels has not changed since the capture of a large portion with the first sensor.

The wristwatch or wristband may include a processor for receiving the images from the sensor or sensors, possibly stitching those images, possibly detect spoofing attempts, and match those images with reference images in order to authenticate or identify the user.

A software module can be stored in a memory of the apparatus and executed by the processor for enhancing the contrast between the blood vessels and the rest of the image.

A software module can be stored in a memory of the apparatus and executed by the processor for removing noise in the image produced by the sensor and/or by the contrast enhancing module.

The different images produced at various wavelengths may be combined into a single image with more information. For example, the shadows and other area of an image in the visible wavelengths which are affected by the ambient light may be corrected with information from the infrared sensor which are less sensible to ambient light. Alternatively, the different images produced at different wavelengths ranges may be compared individually to reference images; in this later case, a decision for the identification/authentication may depend on the results of all classifications at different wavelengths.

The processor may further execute a module for matching a captured image with at least one reference image. In one embodiment, features of the captured image are compared with features of a reference image corresponding to an identity claimed by the user wearing the wrist band. This claimed identity may be for example entered by inputting an identification, possibly with a password, possible on the display of a smartwatch including the sensor, with a device such as a computer, smartphone or tablet connected to the smartwatch. This identity may be claimed for example each time a user starts his watch, or on demand each time he wants to access a protected application or web site for example.

Alternatively, features of the reference image are compared with features of one reference image stored in the smartwatch including the sensor, or in a smart card in this smartwatch. The reference image may be entered during an enrolment session for example when the user uses the sensor for the first time. In this case, the user does not need to claim his identity each time he needs to be authenticated with the biometric sensor; the role of the biometric sensor is mainly to make sure that the wrist band is worn by one authorised user.

In another embodiment, the biometric sensor is used for identifying the wearer of the band, by matching features of his biometric image with features of images corresponding to different users in order to identify which specific user has the wrist band.

The identification or authentication may be performed each time the user starts his apparatus, for example when he puts his watch, when he logs on into the operating system of a smartwatch. It could be performed on demand when the user requests access to a protected application, function or web site for example. It could be performed continuously, or at regular intervals. A plurality of successive images may be used, for example in order to improve the quality and reliability, and/or to detect aliveness of the user and prevent spoofing. In one embodiment, a first authentication is performed when the user put his watch, and a new authentication or confirmation of the previous authentication is performed on request when the user requests access to a protected application, function or web site for example.

The matching of images may comprise a step of aligning them on topographical features. It might comprise a step of extracting features from the captured images, and comparing those features with corresponding features in reference images.

The alignment may use the edges of the wrist, if both edges are visible.

In one example of use, a watch user would place a watch with the sensor on his wrist and secure the clasp, he or she would then move the watch down to stop at the back of the hand where the width of the hand would stop further movement. This stop triggers a change in an accelerometer which starts a clock signal. The user then moves the watch up the wrist to stop at the point where the wrist thickens to prevent any further upward movement. As this movement is taking place the information from the sensor is written into a memory on each clock trigger to provide an image of the wrist.

The invention claimed is:

1. A wristwatch or wristband comprising a biometric sensor, said biometric sensor configured to detect a pattern of wrist blood vessels when the sensor is mounted in the wristband or wristwatch, said sensor comprising a substrate and an array of thermal detectors on said substrate, said thermal detectors comprising near-infrared photodetectors and being configured to capture light reflected by a skin in one or a plurality of wavelengths when in direct contact with the skin or less than 5 mm from the skin, wherein said array comprises organic printed components; and the biometric sensor further comprises at least one light source and a flat plate or foil having upper and lower surfaces configured to internally reflect light, the plate or foil being configured as a light guide to receive and guide light from the light source to the skin;

said wristwatch or wristband further comprising a processor for processing data measured by said sensor in order to identify or authenticate a user, said data representing the pattern of wrist blood vessels of the user;

said wristwatch or wristband still further comprising a software module executable by said processor for causing said processor to stitch data corresponding to different portions of a wrist of the user, in order to retrieve a pattern of blood vessels over an area larger than an area covered by said array of thermal detectors.

2. The wristwatch of wristband of claim 1, said sensor comprising printed transistors on a second substrate, the transistors being connected with the thermal detectors, thereby creating a matrix comprising a plurality of rows and columns of thermal detector cells.

3. The wristwatch of wristband of claim 1, said substrate being flexible.

4. The wristwatch of wristband of claim 1, said substrate being bendable.

5. The wristwatch of wristband of claim 1, said thermal detectors being configured to capture a plurality of images at a plurality of different wavelengths.

6. The wristwatch of wristband of claim 1, wherein the at least one light source is an illumination LEDs or OLEDs produced with thin film technology.

7. The wristwatch of wristband of claim 6, said sensor comprising a pattern of illumination LEDs or OLEDs alternated with photodetectors in a matrix arrangement.

8. The wristwatch of wristband of claim 1, said sensor further comprising an array of optical lenses arranged for focussing light from a distance onto the photodetectors.

9. The wristwatch of wristband of claim 8, said lenses being made of printed elements.

10. The wristwatch of wristband of claim 1, said thermal detectors comprising temperature detectors.

11. The wristwatch or wristband of claim 1, said sensor being mounted on a back of the wristwatch or wristband and configured to detect blood vessels on an outer side of the wrist.

12. The wristwatch or wristband of claim 1, said sensor being mounted on the inner side of a bracelet or clasp and configured to detect blood vessels on an inner side of the wrist.

13. The wristwatch or wristband of claim 1, comprising a software module executable by said processor for causing said processor to retrieve data corresponding to a plurality of successive measures of a wrist of said user and to combine said successive measures, in order to retrieve a pattern of blood vessels over an area larger than an area covered by said array of thermal detectors and/or a more precise pattern of blood vessels.

14. The wristwatch or wristband of claim 1, further comprising a clasp, said clasp comprising the biometric sensor according to claim 1 configured to detect patterns of wrist blood vessels on an inner side of a wrist, said clasp being configured to attach a wristwatch or a wristband to the wrist.

15. The wristwatch of wristband of claim 1, the thermal detectors being near infrared photodetectors or temperature detectors.

16. The wristwatch of wristband according to claim 1, wherein said thermal detectors are configured to capture light reflected by the skin in a plurality of different selectable wavelength ranges.

17. The wristwatch of wristband according to claim 5, said thermal detectors being configured to perform said capture of the plurality of images at the plurality of different wavelengths simultaneously.

18. The wristwatch of wristband according to claim 1, wherein the organic components are digitally printed.

19. The wristwatch of wristband according to claim 18, wherein the organic components are deposited by ink-jet printing.

* * * * *